US00PP27907P3

(12) United States Plant Patent
Kobayashi

(10) Patent No.: US PP27,907 P3
(45) Date of Patent: Apr. 18, 2017

(54) POINSETTIA PLANT NAMED 'PER3112'

(50) Latin Name: ***Euphorbia pulcherrima* Willd.**
Varietal Denomination: PER3112

(71) Applicant: Ruth Kobayashi, Carlsbad, CA (US)

(72) Inventor: Ruth Kobayashi, Carlsbad, CA (US)

(73) Assignee: Dümmen Group B.V., De Lier (NL)

( * ) Notice: Subject to any disclaimer, the term of this patent is extended or adjusted under 35 U.S.C. 154(b) by 125 days.

(21) Appl. No.: 14/545,496

(22) Filed: May 12, 2015

(65) Prior Publication Data

US 2016/0338240 P1 Nov. 17, 2016

(51) Int. Cl.
*A01H 5/02* (2006.01)

(52) U.S. Cl.
USPC ..... Plt./304

(58) Field of Classification Search
USPC ..... Plt./263.1, 302, 303, 304
See application file for complete search history.

*Primary Examiner* — Susan McCormick Ewoldt
*Assistant Examiner* — Karen Redden
(74) *Attorney, Agent, or Firm* — C. A. Whealy

(57) ABSTRACT

A new and distinct cultivar of Poinsettia plant named 'PER3112', characterized by its compact, uniform, upright and mounded plant habit; moderately vigorous growth habit; freely and upright branching habit; dark green-colored leaves; under natural season conditions, plants flower on or about November 7 in Southern California; large inflorescences with creamy white-colored flower bracts; and good post-production longevity.

2 Drawing Sheets

Botanical designation: *Euphorbia pulcherrima* Willd.
Cultivar denomination: 'PER3112'.

BACKGROUND OF THE INVENTION

The present invention relates to a new and distinct cultivar of Poinsettia plant, botanically known as *Euphorbia pulcherrima* Willd., and hereinafter referred to by the cultivar name 'PER3112'.

The new Poinsettia plant is a product of a planned breeding program conducted by the Inventor in Encinitas, Calif. The objective of the breeding program is to create new uniform Poinsettia plants having large inflorescences with attractive flower bracts and excellent post-production longevity.

The new Poinsettia plant is a naturally-occurring whole plant mutation of a proprietary selection of *Euphorbia pulcherrima* Willd. identified as code number 7-10, not patented. The new Poinsettia plant was discovered and selected by the Inventor from within a population of plants of the mutation parent in a controlled greenhouse environment in Encinitas, Calif. on Nov. 25, 2011.

Asexual reproduction of the new Poinsettia plant by terminal vegetative cuttings in a controlled greenhouse environment in Encinitas, Calif. since January, 2012 has shown that the unique features of this new Poinsettia plant are stable and reproduced true to type in successive generations of asexual reproduction.

SUMMARY OF THE INVENTION

Plants of the new Poinsettia have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'PER3112'. These characteristics in combination distinguish 'PER3112' as a new and distinct Poinsettia plant:

1. Compact, uniform, upright and mounded plant habit.
2. Moderately vigorous growth habit.
3. Freely and upright branching habit.
4. Dark green-colored leaves.
5. Under natural season conditions, plants flower on or about November 7 in Southern California.
6. Large inflorescences with creamy white-colored flower bracts.
7. Good post-production longevity.

In side-by-side comparisons conducted in Encinitas, Calif., plants of the new Poinsettia differ primarily from plants of the mutation parent selection in flower bract color as plants of the mutation parent selection have bright red-colored flower bracts with pink-colored flecks.

Plants of the new Poinsettia can be compared to plants of the *Euphorbia pulcherrima* Willd. 'Peterstar White', disclosed in U.S. Plant Pat. No. 9,878. In side-by-side comparisons conducted in Encinitas, Calif., plants of the new Poinsettia differed primarily from plants of 'Peterstar White' in the following characteristics:

1. Plants of the new Poinsettia were more compact than plants of 'Peterstar White'.
2. Plants of the new Poinsettia had a more upright branching habit than plants of 'Peterstar White'.
3. Plants of the new Poinsettia had darker green-colored leaves than plants of 'Peterstar White'.
4. Plants of the new Poinsettia flowered about 20 days earlier than plants of 'Peterstar White'.
5. Plants of the new Poinsettia and 'Peterstar White' differed in flower bract color as plants of 'Peterstar White' had light lemon white-colored flower bracts.

Plants of the new Poinsettia can be compared to plants of the *Euphorbia pulcherrima* Willd. 'PER10606', disclosed in U.S. Plant Pat. No. 20,351. In side-by-side comparisons conducted in Encinitas, Calif., plants of the new Poinsettia differed primarily from plants of 'PER10606' in the following characteristics:

1. Plants of the new Poinsettia were more compact than plants of 'PER10606'.
2. Plants of the new Poinsettia had a more upright branching habit than plants of 'PER10606'.

BRIEF DESCRIPTION OF THE PHOTOGRAPHS

The accompanying photographs illustrate the overall appearance of the new Poinsettia plant showing the colors as true as it is reasonably possible to obtain in colored reproductions of this type. Colors in the photographs may differ slightly from the color values cited in the detailed botanical description which accurately describe the colors of the new Poinsettia plant.

The photograph on the first sheet is a side perspective view of a typical flowering plant of 'PER3112' grown in a container.

The photograph on the second sheet is a close-up view of a typical flowering plant of 'PER3112'.

DETAILED BOTANICAL DESCRIPTION

Plants used in the aforementioned photographs and in the following detailed description were grown during the late autumn/early winter in 16.5-cm containers in a polyethylene-covered greenhouse in Encinitas, Calif. and under natural season conditions and cultural practices typical of commercial Poinsettia production. During the production of the plants, day temperatures averaged 26° C., night temperatures averaged 18° C. and light levels averaged 5,000 foot-candles. Measurements and numerical values represent averages for typical flowering plants. Plants were pinched one time and were 21 weeks old when the photographs and the description were taken. In the following description, color references are made to The Royal Horticultural Society Colour Chart, 2007 Edition, except where general terms of ordinary dictionary significance are used.

Botanical classification: *Euphorbia pulcherrima* Willd. 'PER3112'.

Parentage: Naturally-occurring whole plant mutation of a proprietary selection of *Euphorbia pulcherrima* Willd. identified as code number 7-10, not patented.

Propagation:

*Type*.—Terminal vegetative cuttings.

*Time to initiate roots*.—About seven to ten days at night temperatures about 20° C. and day temperatures about 27° C.

*Time to produce a rooted young plant*.—About four weeks at night temperatures about 20° C. and day temperatures about 27° C.

*Root description*.—Fibrous; white in color.

Plant description:

*Plant habit and form*.—Compact, uniform, upright and mounded plant habit; inverted triangle; large inflorescences positioned above the foliar plane; moderately vigorous growth habit.

*Plant height*.—About 41.5 cm.

*Plant diameter or spread*.—About 52 cm.

*Lateral branch description*.—Quantity: Freely branching habit, about seven lateral branches develop after pinching; upright branching habit. Length: About 34 cm. Diameter: Thick, about 9 mm. Internode length: About 2.2 cm. Strength: Strong. Aspect: About 30° to 40° from vertical. Texture: Smooth, glabrous. Luster: Glossy. Color: More green than 146A.

*Leaf description*.—Arrangement: Alternate, simple. Length: About 11.5 cm. Width: About 8.25 cm. Shape: Ovate. Apex: Acuminate. Base: Mostly truncate. Margin: Mostly entire, occasionally with shallow dentations and/or serrations. Aspect: Flat. Venation pattern: Pinnate, arcuate. Texture, upper and lower surfaces: Smooth, glabrous; slightly rugose. Color: Developing and fully expanded leaves, upper surface: Darker green than N137A or 147A; venation, close to 146A. Developing and fully expanded leaves, lower surface: Close to N137B to N137C; midvein, close to 146B to 146C and lateral veins, close to 146B. Petioles: Length: About 7.5 cm. Diameter: About 4 mm. Texture, upper and lower surfaces: Smooth, glabrous. Luster, upper and lower surfaces: Glossy. Color, upper and lower surfaces: Close to 146B to 146C.

Inflorescence description:

*Inflorescence type and habit*.—Terminal inflorescences are compound corymbs of cyathia with colored flower bracts subtending the cyathia; inflorescences uniformly positioned above the foliar plane.

*Fragrance*.—None detected.

*Flowering response*.—Under natural season conditions, plants typically flower on or about November 7 in Southern California; under artificial long nyctoperiod/short photoperiod conditions, plants flower about seven to eight weeks later.

*Post-production longevity*.—Good post-production longevity; plants of the new Poinsettia maintain good substance and flower bract color for about four to six weeks under interior conditions; flower bracts persistent and cyathia not persistent.

*Inflorescence diameter*.—About 30.5 cm.

*Inflorescence height* (*depth*).—About 4.5 cm.

*Flower bracts*.—Quantity per inflorescence: About 24. Length, largest bracts: About 12.5 cm. Width, largest bracts: About 10 cm. Shape: Ovate. Apex: Acuminate. Base: Truncate. Margin: Entire, occasionally with shallow dentations and/or serrations. Texture, upper and lower surfaces: Smooth, glabrous; satiny; mostly flat, keeled and somewhat rugose. Aspect: Upright to horizontal. Venation pattern: Pinnate, arcuate. Color: Developing or transitional bracts, upper surface: Ground color, close to 144A; irregular and random patches, close to 5C and 5D. Developing or transitional bracts, lower surface: Ground color, close to 144B; irregular and random patches, close to 5D. Fully expanded bracts, upper surface: Close to 6D and 162C to 162D; color becoming closer to 11B and 10C with development. Fully expanded bracts, lower surface: Close to 162C to 162D, 5D and 6D; color becoming closer to 11B and 10C with development. Bract petioles: Length: About 3.2 cm. Diameter: About 3.5 mm. Texture, upper and lower surfaces: Smooth, glabrous. Color, upper and lower surfaces: Close to 144B.

*Cyathia*.—Quantity per corymb: About 16 to 18. Length: About 8 mm. Width: About 4 mm. Shape: Oval. Texture: Smooth, glabrous. Color, inner and outer surfaces: Close to 144A.

*Nectaries*.—Quantity per cyathium: One. Length: About 6 mm. Width: About 3.5 mm. Shape: Roughly oval. Texture: Smooth, glabrous. Color, inner and outer surfaces: Close to 17B to 17C.

*Peduncles*.—Length: About 3.5 mm. Diameter: About 2 mm. Strength: Strong. Aspect: Mostly upright. Texture: Smooth, glabrous. Color: Close to 144A.

*Reproductive organs*.—Stamens: Quantity per cyathium: About 20. Filament length: About 5 mm. Filament color: Close to 154D. Anther shape: Round; bi-lobed. Anther length: Less than 1 mm. Anther color: Close to 9A. Amount of pollen: None observed. Pistils: Quantity per cyathium: One; tri-parted. Pistil length: About 7.5 mm. Stigma shape: Lanceolate, recurved. Stigma color: Close to 3C to 3D. Style length: About 4 mm. Style color: Close to 144A. Ovary color: Close to 144A.

*Seeds and fruits*.—Seed and fruit production have not been observed on plants of the new Poinsettia.

Disease & pest resistance: Plants of the new Poinsettia have not been shown to be resistant to pathogens and pests common to Poinsettia plants.

Temperature tolerance: Plants of the new Poinsettia have been observed to tolerate temperatures ranging from about 16° C. to about 29° C.

It is claimed:

1. A new and distinct Poinsettia plant named 'PER3112' as illustrated and described.

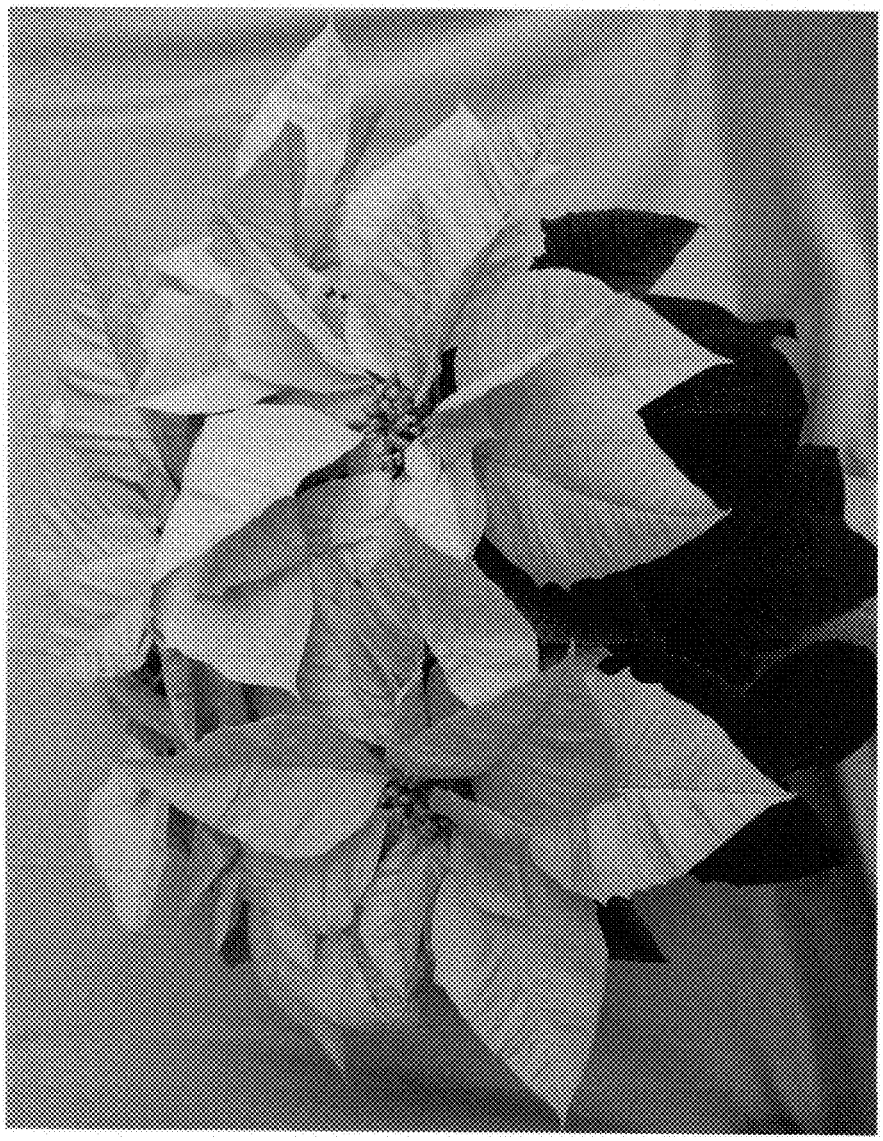

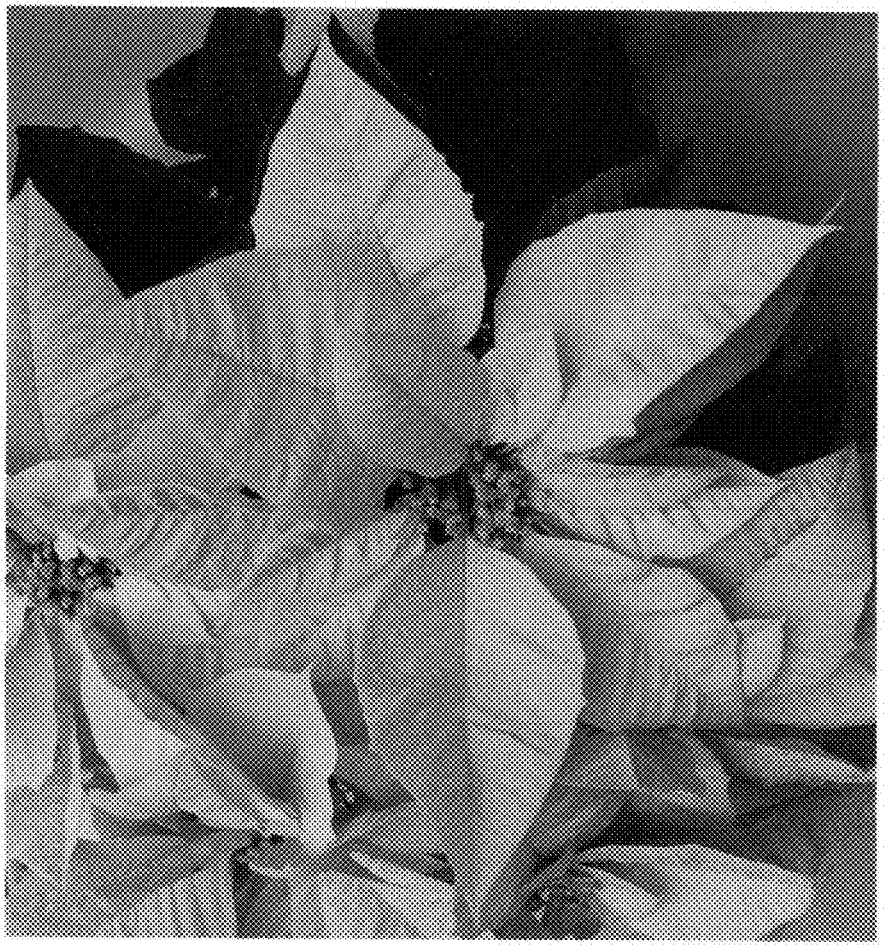

* * * * *